(12) United States Patent
Farrell

(10) Patent No.: US 12,364,829 B2
(45) Date of Patent: Jul. 22, 2025

(54) ORAL APPLIANCE

(71) Applicant: Myosa Pty Ltd, Helensvale (AU)

(72) Inventor: Christopher John Farrell, Helensvale (AU)

(73) Assignee: Myosa Pty Ltd, Helensvale (AU)

( * ) Notice: Subject to any disclaimer, the term of this patent is extended or adjusted under 35 U.S.C. 154(b) by 390 days.

(21) Appl. No.: 17/259,531

(22) PCT Filed: Jul. 19, 2019

(86) PCT No.: PCT/AU2019/050757
§ 371 (c)(1),
(2) Date: Jan. 11, 2021

(87) PCT Pub. No.: WO2020/014748
PCT Pub. Date: Jan. 23, 2020

(65) Prior Publication Data
US 2021/0162156 A1  Jun. 3, 2021

(30) Foreign Application Priority Data

Jul. 20, 2018  (AU) ................................ 2018902632

(51) Int. Cl.
*A61F 5/56* (2006.01)
*A61M 16/04* (2006.01)
*A61M 16/06* (2006.01)

(52) U.S. Cl.
CPC .......... *A61M 16/0493* (2014.02); *A61F 5/56* (2013.01); *A61F 5/566* (2013.01); *A61M 2016/0661* (2013.01); *A61M 2207/00* (2013.01)

(58) Field of Classification Search
CPC ...... A61F 5/56; A61F 5/566; A61F 2005/563; A61F 5/58; A61C 7/08; A61M 16/049;
(Continued)

(56) References Cited

U.S. PATENT DOCUMENTS 2,669,988 A * 2/1954 Carpenter ................. A61B 1/24
128/861
2,882,893 A * 4/1959 Nicholas ........... A61M 16/0495
128/861

(Continued)

FOREIGN PATENT DOCUMENTS

AU     2017265041 A1   12/2017
EP        1203570 A2    5/2002
(Continued)

OTHER PUBLICATIONS

PCT/AU2019/050757 International Search Report and Written Opinion mailed Sep. 16, 2019, 13 pages.
(Continued)

*Primary Examiner* — Camtu T Nguyen
(74) *Attorney, Agent, or Firm* — Cozen O'Connor

(57) ABSTRACT

An oral appliance for the treatment of sleep disorder breathing in a patient has a U shaped appliance body with a front section and two arms. The appliance body has an inner wall and an outer wall, and a web interconnects the inner and outer walls forming an upper dental arch receiving channel. The front section of the body has an air inlet opening for taking in air during inhalation. The oral appliance also has an air outlet member with an air outlet and an air flow passageway connecting the air inlet opening with the air outlet.

21 Claims, 18 Drawing Sheets

(58) Field of Classification Search
CPC .......... A61M 16/0493; A61M 16/0495; A61M 16/0497; A61M 16/0488
See application file for complete search history.

(56) References Cited

U.S. PATENT DOCUMENTS

| | | | | |
|---|---|---|---|---|
| 4,112,936 | A | * | 9/1978 | Blachly ............. A61M 16/0493 128/207.14 |
| 4,270,531 | A | * | 6/1981 | Blachly ............. A61M 16/0495 128/207.14 |
| 6,055,986 | A | | 5/2000 | Meade |
| 6,269,816 | B1 | * | 8/2001 | Rigonatti .......... A61M 16/0488 128/200.26 |
| 6,259,988 | B1 | | 10/2001 | Galkowski |
| 7,004,172 | B1 | | 2/2006 | Zacco |
| D1,012,290 | S | * | 1/2024 | Farrell ......................... D24/180 |
| 2003/0015198 | A1 | * | 1/2003 | Heeke ............... A61M 16/0495 128/200.24 |
| 2006/0102711 | A1 | | 5/2006 | Gavish |
| 2007/0149891 | A1 | | 6/2007 | George et al. |
| 2008/0076094 | A1 | | 3/2008 | Hindin |
| 2008/0236597 | A1 | | 10/2008 | Bergersen |
| 2008/0257358 | A1 | | 10/2008 | Stern et al. |
| 2009/0241969 | A1 | * | 10/2009 | Walker .................. A61F 5/566 128/848 |
| 2010/0018538 | A1 | | 1/2010 | Sotos |
| 2010/0196837 | A1 | | 8/2010 | Farrell |
| 2011/0168188 | A1 | | 7/2011 | Moore et al. |
| 2012/0186589 | A1 | | 7/2012 | Singh |
| 2014/0261450 | A1 | | 9/2014 | Morehead |
| 2015/0157821 | A1 | * | 6/2015 | Manecke ............... A61B 13/00 600/114 |
| 2016/0287831 | A1 | | 10/2016 | Tebbutt et al. |
| 2017/0209300 | A1 | | 7/2017 | Radman |
| 2018/0085247 | A1 | | 3/2018 | Trainor et al. |
| 2018/0116863 | A1 | | 5/2018 | Shah et al. |
| 2018/0360646 | A1 | * | 12/2018 | Bedford .................. A61F 5/566 |

FOREIGN PATENT DOCUMENTS

| | | | |
|---|---|---|---|
| WO | WO 1994023674 | A1 | 10/1994 |
| WO | WO 2012155214 | A1 | 11/2012 |
| WO | WO 2015/123718 | A1 | 8/2015 |
| WO | WO 2015/149127 | A1 | 10/2015 |
| WO | WO 2016/187646 | A1 | 5/2016 |
| WO | WO 2016209184 | A1 | 12/2016 |
| WO | WO 2017/020079 | A1 | 2/2017 |
| WO | WO 2017165918 | A1 | 10/2017 |
| WO | WO 2018/098527 | A1 | 7/2018 |
| WO | WO 2019/051545 | A1 | 3/2019 |

OTHER PUBLICATIONS

European Patent Application No. 19837782.2 extended search and opinion dated Jan. 7, 2022, 8 pages.

* cited by examiner

ORAL APPLIANCE

FIELD

The present disclosure relates broadly to an oral appliance for use in the treatment of sleep disorder breathing (SDB).

Definitions

In the specification and claims the term "comprising" shall be understood to have a broad meaning similar to the term "including" and will be understood to imply the inclusion of a stated integer or step or group of integers or steps but not the exclusion of any other integer or step or group of integers or steps. This definition also applies to variations on the term "comprising" such as "comprise" and "comprises".

In the specification and claims, the term "sleep disorder breathing" (SBD) refers to any condition where there is an abnormal breathing pattern during sleep. In some cases this abnormality is as a result of an upper airway obstruction during sleep, including but not limited to include snoring, upper airway resistance syndrome (UARS), and obstructive sleep apnea-hypopnea (OSA). Abnormal breathing can also occur in the absence of any airway obstruction during sleep in which the patient stops breathing for a period of time, known as an apneic event.

BACKGROUND

Over the past two decades, the medical and dental profession has become more aware of breathing disorders and in particular sleep disorder breathing as a major contributor to a number of health problems. Previously it was considered that snoring was a manifestation of a sleeping habit but it is now known that this leads to more severe disorders like Obstructive Sleep Apnea (OSA). OSA has been associated with the causes of heart disease, strokes and all as chronic daytime tiredness and spontaneous sleeping. The various forms of severity of OSA, snoring, and other syndromes have been described under the definition Sleep Disorder Breathing (SDB).

SDB comprises a wide spectrum of sleep-related breathing abnormalities; those related to an increase in upper airway resistance include snoring, upper airway resistance syndrome (UARS), and obstructive sleep apnea-hypopnea (OSA). Many clinicians regard SDB as a spectrum of diseases. This concept suggests that a person who snores may be exhibiting the first manifestation of SDB and that snoring should not be viewed as normal. This concept has support from experimental studies showing increasing airway collapsibility during sleep with progression from normal, snoring, UARS, and OSA.

Snoring is one of the most common aspects of SDB. After sleep apnea syndrome was recognized, snoring began to be viewed as an important clinical symptom. Although it is by far the most common symptom of sleep apnea, not all patients who snore have sleep apnea.

Pathogenesis of OSA involves a combination of reduced upper airway size and altered upper airway muscle activity, which causes oral tissue to collapse, and hence a blockage to occur. When a person is awake, muscles hold the pharyngeal airway open. These muscles can relax when sleeping. Other factors which are thought to contribute to OSA include weight, tongue size, soft palate volume, a retrognathic mandible, an anteroposterior discrepancy between the maxilla and the mandible, and obesity.

Snoring and OSA are often associated as generally both are caused by blockage of the pharyngeal airway by, for example, excess tissue when various muscles of the body, including the tongue, relax. As the tongue relaxes, it moves posteriorly, blocking the pharyngeal airway. When the pharyngeal airway is blocked, exhaled air is forced through the airway with increased velocity thereby causing vibration of the tongue, tissue, or other obstruction, thereby creating noise.

Snoring is caused by the partial obstruction of breathing during sleep while OSA occurs when the tongue and soft palate collapse onto the back of the throat and completely block the pharyngeal airway, thereby stopping breathing during sleep and restricting the flow of essential oxygen. Thus, a correlation between snoring and OSA is generally recognized in the medical community.

Snoring is common in people who breathe through their mouth when asleep. Mouth breathing causes the mandible to drop and decreases the area of the pharyngeal airway. It also causes the tongue to be pushed back into the throat, thereby creating the obstruction associated with SDB.

The traditional medical treatment for OSA has been the Continuous Positive Air Pressure Appliance (CPAP). CPAP treatment uses a positive air pressure to blow air through the nose and into the upper airways so as to prevent upper airway collapse during sleep. The positive air pressure is generated by a pump and is applied through a small mask which fits over the nose, nasal pillows or a mask that fits over the nose and mouth.

When pressure is applied to the nose, the uvula and soft palette partially block off the mouth. Some air may escape through the mouth, but if the mouth is kept closed a seal can be obtained. Air leaking through the mouth is known as "mouth leak" and is uncomfortable for the user. Mouth leak leads to a large unidirectional flow of air through the nose and out through the mouth driven by the positive air pressure of the CPAP. In some people this can cause an increase in nasal mucosal blood flux, mucosal drying and rebound congestion. CPAP humidification can generally avoid these problems.

Full face (oronasal) masks may be used to assist with mouth leak. Alternatively chinstraps may be used to hold the mouth closed. Neither solution is conducive to a comfortable night's sleep. Also, the tighter the full face mask, the more the mandible is forced back into the airway as well as compromising the tongue position. This makes the SDB and OSA worse. The problem is well known with the treatment of OSA.

It is important that the CPAP masks provide a good seal against the face and are kept firmly in place by head straps. In practice, this is uncomfortable and often results in poor compliance. Some patients feel claustrophobic whilst wearing masks. For this reason nasal only masks are preferred, but suffer from either mouth leak or inefficiency if the patient has a nasal obstruction.

Many patients cannot tolerate CPAP when their nasal breathing is obstructed. This may be due to a number of factors including nasal or sinus structure abnormalities like a deviated septum, swollen turbinates and problems with the upper palate and nasal congestion.

CPAP can have undesirable side effects that also lead to non-compliance or intolerance. Such side effects include nasal irritation that can cause congestion and mucosal dryness. This can lead to patients unconsciously taking off the mask prematurely. Nasal irritation is exacerbated by mouth leak.

Poor adherence or compliance (30-60%) to CPAP is a recognized limiting factor in treating OSA, leaving patients at risk for co-morbid conditions and impaired quality of life. Compliance to CPAP therapy is defined as CPAP for at least 4 hours for 70% of nights. This definition alone has an inherent non-compliance factor built in, as it would be optimal for the CPAP treatment to be used for the entire sleeping period to limit apnea and hypopnea events.

In conclusion, the CPAP treatment that is now widely used has many inherent disadvantages, but is accepted as the best that can be done for the SDB patient.

Alternatives for patients who are non-compliant include the use of intra-oral appliances or Dental Sleep Appliances (DSA).

DSAs for alleviation of SDB symptoms are considered less effective than CPAP and not suitable for more severe cases. However, they are more convenient, easier to use and certainly more portable. The compliance factor has brought the attention of the medical profession to view DSA's as the primary treatment for SDB for moderate to more severe cases who have a compliance issue with the CPAP regime.

There are many types of DSAs and the designs vary considerably. The most common are the Mandibular Advancement Devices (MAD). The principle behind the MAD devices is that advancing the mandible in an anterior position relative to the maxilla during sleep opens the pharyngeal airway by indirectly urging the tongue forward to stimulate activity of the muscles in the tongue and thereby also increases the forward rigidity of the tongue. Since the tongue attaches to the posterior portion of the mandibular symphysis, advancing the mandible forward relative to the maxilla also pulls the tongue forward, thus preventing the tongue from obstructing the pharyngeal airway. MADs therefore function to move the mandible, and hence the tongue forward to open the oropharynx. Snoring is believed to decrease proportionally with the increase in airway size or diameter.

Other MAD devices are in two parts that are hinged that are adjustably connectable to allow for titration of the amount of advancement. Others are formed from a single piece of thermoplastic with a living hinge. A recognized advantage of the hinged devices is that they allow the mouth to open for unrestricted breathing. It is considered very important that breathing is not restricted for mouth breathers as the object of the prior art MAD devices is to increase the amount of airflow.

Other devices are known as tongue retaining devices that work by pulling the tongue forward so as to open the airway, with less or no mandibular advancement when compared with the MAD devices. It will be appreciated that by pulling the tongue forward, it is also not possible to mouth breath and/or many devices block the mouth completely. Such devices are uncomfortable and have poor compliance. Further they are completely unsuitable for patients with nasal obstruction, congestion or irritation.

However, these MAD devices pose potentially damaging effects. Most single piece devices fit over both the maxillary and mandibular teeth and are typically held nearly stationary, thereby restricting movement, causing discomfort, and potential permanent repositioning of the jaw.

The temporomandibular joint (TMJ) is the joint that connects the mandible to the skull. The mandibular condyle is received within the superior synovial cavity The TMJ is flexible, allowing the mandible to move smoothly up and down and side to side and enabling a person to talk, chew and yawn. Muscles attached to and surrounding the TMJ control the position and movement of the mandible.

Continued use of devices that restrict the natural lateral movements as well as anterior and posterior movement of the mandible can potentially aggravate the TMJ and the related facial musculature.

Still further, mandibular advancement will clearly place stress on the TMJ as the mandibular condyle is anteriorly displaced relative to its normal position. This can lead to TMJ disorder. TMJ disorder covers a group of conditions that cause pain and dysfunction in the jaw joint and the muscles that control jaw movement.

There are therefore serious concerns within the dental community of the medium to long term effects of devices that over advance the mandible. These effects can cause adverse changes in occlusion, damage teeth and potential damage to the TMJ's. However, it is thought that the high priority in correcting snoring, SDB and health issues from OSA would make the medical practitioner and patient consider this a side effect that needs to be accepted for the overall benefits.

Patients with existing TMJ disorders are generally cautioned against using a MAD as such use can exacerbate the condition. A healthy TMJ is a prerequisite for MAD use. MADs are based on orthodontic appliance principles which are designed to correct a class II malocclusion. In a class II malocclusion there is a misalignment between the teeth of the dental arches and the upper teeth are forward of the lower teeth in what is commonly known as an overbite. Orthodontic appliances for the treatment of class II malocclusions in pre-adolescents advance the mandible and stimulate and enhance mandibular growth. The appliances also place and equal and opposite retractive force on the maxilla and restrains growth of the maxilla.

It is generally believed that the greater level of mandibular advancement caused by a MAD, the better the treatment effective for SDB. Advancement of between 50% and 75% of maximum mandibular protrusions is recommended. Physiological protrusion lengths are typically between about 7 mm to about 12 mm. The American Academy of Dental Sleep Medicine (AADSM) has published a report on what features define an effective oral appliance for the treatment of OSA. One of the features defined is that the appliance should permit protrusive advancement over a range of at least 5 mm. It is considered desirable to be able to gradually advance the mandible with treatment so as to reduce pain and soreness and alleviate TMJ pain.

These recommendations have been based upon a number of factors and in particular pulse oximetry. Oximetry measures hemoglobin $O_2$ saturation. This measurement is based upon the generally held belief in the MAD art that simply physically opening up the airways and allowing more air to be breathed can treat SDB.

It may be appreciated that using an oral appliance designed for treating a class II malocclusion by advancing the mandible and retracting the maxilla would have the same effect on a person with normal occlusion.

It is the maxilla that determines the effective horizontal dimension of the pharynx and in particular the upper pharynx. Maxillary constriction has been reported to be associated with narrowing of the pharyngeal airway and may play a role in the etiology of OSA. Surgical maxillary expansion is an effective procedure for widening nasal cavities and decreasing nasal airway resistance which can lead to improvement in nasal breathing.

More recently, a modification to a conventional MAD was described in Australia Patents Numbers AU2012255625 and AU2015240431. The disclosed MAD's have a rigid U shaped body and an air inlet/outlet opening extending from the front of the U to allow for mouth breathing. The body has enclosed channels extending from the inlet at the front along the full length of the arms so as to in each arms that extend from the front to deliver inhaled air from the inlet to the posterior of the oral cavity in the vicinity of a junction between the hard and soft pallets. In this way, obstruction of the airway by the tongue or other soft tissue is bypassed.

The appliance has a lingual flange for engaging mandibular teeth for mandibular advancement. The appliance is considered to be particularly suitable for patients with nasal congestion or obstruction who are intolerant of CPAP.

WO2015/149127 describes a similar device in which the lingual flange is moveable by a screw device such that the degree of mandibular displacement can be titrated.

WO2017/020079 also describes a similar device to that above and further includes a removable tongue retainer for holding the tongue forward between the teeth.

WO2017/165918 further describes a device having air channels for delivering air to the posterior of the oral cavity. In this disclosure, the body is made in two parts connected via an adjustment mechanism so as to adjust the degree of mandibular displacement.

Each of the appliances described in the above patent documents must be custom made specifically for each individual. 3D scanning of the mouth of a user is described. The scanned information is then used to manufacture a customized device by additive manufacturing such as 3D printing of a metallic material such as titanium or stainless steel. Electron beam melting (EBM) is a technique that is specifically mentioned. This technique uses electron beams to build up metal powders layer by layer. The metal bodies are encased in a soft plastics material.

It is important that the enclosed channels that pass through the arms of the appliance are able to deliver a sufficient and uninterrupted flow of air to the posterior of the oral cavity. The rigid titanium body ensures that this occurs. The rigidity of the body also means that accurate scanning of a user's mouth must be made to ensure an accurate fit, comfort and compliance.

Conventional non-customized DSAs are injection molded from a flexible thermoplastics material such as ethylene vinyl acetate (EVA) that softens below 100° and is therefore self mouldable to a user's dentition. When moulding a user presses the teeth on the softened EVA. If air channels were in the arms of the body between the teeth there is a risk of distortion of the channels that may compromise uniformity of air flow.

It will be also appreciated that 3D scanning and custom manufacturing of the appliances by 3D printing of titanium as described above is time consuming and expensive. It follows that appliances manufactured thereby may be unavailable to many SDB sufferers.

SUMMARY

It has been appreciated that there is a desire for a less expensive appliance that may not need to be custom made and/or may provide the public with a useful choice.

The present disclosure therefore relates to an oral appliance for the treatment of sleep disorder breathing in a patient, the oral appliance comprising;
a U shaped appliance body with a front section and two arms, the appliance body including an inner wall and an outer wall,
a web interconnecting the inner wall and the outer wall so as to define an upper dental arch receiving channel;
an air inlet opening for intake of air during inhalation;
an air outlet member configured in use to locate above the tongue with an air outlet for directing inhaled air between the tongue and the hard palette towards the posterior oral cavity; and
an air flow passageway between the air inlet opening and the air outlet member.

The oral appliance body is suitably manufactured from a soft and/or resilient material, suitably a thermoplastics material.

The oral appliance body, and in particular the arms suitably has a degree of compliance such that the oral appliance can be fitted to patient's with different size dental arches.

The thermoplastics material may soften at temperatures below 100° such that it is user mouldable. Such materials include ethylene vinyl acetate (EVA) that allows a user to soften the device in hot water and mould the device about the user's teeth as is well known with mouth guards. The oral apparatus may also have a core or frame from material that does not soften below 100° C. so as to provide structural support to the appliance.

Alternatively the oral appliance may be formed from a soft thermoplastics material that does not soften below 100° soft polymer but is soft and compliable at room temperature such as polyurethane or silicone. This may be compared to known oral appliances such as the MADs that are made from injection moulded ethylene vinyl acetate (EVA) or liquid silicon rubber (LSR).

Silicone is particularly suitable as it is pliable and does not require moulding to a user's teeth. This may improve comfort; allow the user some jaw movement that will also contribute to user comfort and thus compliance.

Suitably the oral appliance may be made by Slicone or other material by injection moulding. All the described appliances are injection moulded. EVA PU and LSR. So this needs to be technically a bit clearer.

The appliance body may be made in a number of different stock sizes so that a majority of the population can select an appliance that can be fitted over their upper arch with a reasonable fit.

The oral appliance has an air inlet opening and an air outlet. As will be described below, the disclosed oral appliance delivers air into the oral cavity with minimal interference from the tongue. For this reason, the terms inlet and outlet are used to describe the air flow direction when inhaling. The opposite flow direction occurs when exhaling.

The oral appliance is U shaped with an air inlet opening at the front so as to allow for mouth breathing. The air inlet may be any suitable shape or configuration. Suitably the air inlet has a cross sectional area for breathing that allows a patient to breathe fully through the mouth. This may be important for patients with nasal obstruction. The oral appliance also allows a person to partially breathe through the nose.

The air inlet opening may be formed in the front of the appliance body.

In another embodiment, the appliance comprises an air inlet member that extends forward of the front of the appliance body such that the air inlet opening is spaced from the body and the air inlet member forms part of the air flow passageway between the air inlet opening and the air outlet.

The air inlet member body may also define part of the air flow passageway.

Suitably the air inlet member is configured so as to allow a patient's lips to form a lip seal about the air inlet member. This prevents air from entering the oral cavity directly through the mouth rather than through the air inlet. In one aspect, the air inlet member has an elliptic cylindrical shape.

In another aspect, the air inlet member has an elliptic frustoconical shape with side walls that taper from the air inlet opening towards the appliance body.

The oral appliance has an air outlet member with a body that in use locates above the tongue and directs inhaled air between the tongue and the hard palette towards the posterior of the oral cavity and in particular the pharyngeal airway.

Suitably the air outlet member is configured that in use the air outlet delivers air at a location along a line extending between the anterior teeth and the molar region.

Suitably the air outlet member is configured to abut or be positioned close to the hard palette. Suitably the air outlet member has a degree of reliance such that it resiliently contacts or presses against the hard palette. This may assist in directing air flow above the tongue during inhalation so as to avoid obstruction thereby. It may also create a seal with the hard palette so as to prevent or minimise air passing above the air inlet member during exhalation to assist in directing air into the air outlet.

Suitably the air flow passageway between the air inlet and air outlet member includes a passageway part that is constricted with respect to the air outlet member.

Fluid flow through an abrupt constriction in a pipe results in a decrease in pressure of the fluid. Fluid flow also experiences a decrease in pressure when travelling through a bend in a pipe. Fluid pressure also drops when fluid flows through an abrupt expansion.

Whilst not wishing to be bound by theory, it is believed that the flow of air upon inhalation from the inlet member through the constricted part, bend in the constricted part and from the air outlet into the oral cavity experiences a decrease in pressure. This decrease in pressure results in a positive external pressure that may assist inhalation.

Suitably, the oral cross sectional flow area of the air inlet member before the constricted part may be between about 200 mm. to about 400 mm.

The cross sectional flow area of the constricted part may be between about 50 mm and about 100 mm.

Suitably, the oral appliance is configured to encourage the tongue into a forward position that corresponds to the natural resting position. When the tongue is in the natural resting position, the tip positions on the incisal papilla at the anterior part of the upper palate. With the tip of the tongue in this position, the dorsum of the tongue runs at the cervical third of the crowns and roots of the upper premolars. The base of the tongue goes downward at the molars, leading to insert at the hyoid bone. When the tip of the tongue is at its physiological position, its dorsum and base tend to reposition at their physiological positions as well, with the base descending at the molar area.

However, when mouth breathing, the tongue is in a lowered position to allow the patient to more easily breathe through the mouth. A disadvantage of this position is that the lowered tongue may partially block the airway.

The tip of the tongue is highly sensitive and haptically explores objects in the mouth and provides perception of size and shape of objects in the mouth. This is important for mastication and swallowing. The presence of the air outlet member in the oral cavity will generally evoke a spontaneous response for the tongue to find its way towards to touch and explore the air outlet member.

The arrangement of the air outlet member located above the tongue that directs air above the tongue allows the patient to inhale and exhale through the air inlet opening with the tongue in the elevated position.

The oral appliance may further comprise a lower dental arch receiving channel and the upper and lower dental arch receiving channels may be configured so that when the oral appliance is worn in the mouth, the patient's mandible is advanced. This further brings the tongue forward and may alleviate any obstruction of the pharyngeal airway.

Still further, the airflow generally bypasses saliva ducts such that mouth dryness is reduced or alleviated.

As discussed in the introductory section, there are a number of disadvantages with conventional MAD devices. It is generally believed that the further the mandibular advancement, the more effective is the MAD device. Generally mandibular advancement of between about 7 mm to about 12 mm is recommended.

On the other hand, in the present appliance, the tongue has already been voluntarily brought forward in view of the presence of the tongue such that less physical mandibular advancement may be required. For example, mandibular displacement of about 5 mm or less or between about 1 mm to about 3 mm may be sufficient.

It will be appreciated that this lesser degree of displacement, will provide less strain on the TMJ and less retractive action of the maxilla.

The web suitably thickens from the front of the web to a point towards the trailing ends of the arms. This tends to fill in the space between the teeth of the upper and lower jaw. This in some respects resembles an airfoil and thickens the web. This arrangement puts more pressure on the rear molars thereby relaxing and exercising the joints and muscles.

Suitably, the thickened portions of the web are compressible. Compression may be achieved by providing a section of softer or more compressible material. Suitably compression is achieved by providing one or more holes through the trailing ends of the arms of the web.

The combination of the airfoil shape and the ability to compress that part of the web between the rear molars can alleviate TMJ pain and other discomfort that is felt by users of conventional rigid devices.

Further still the ability to compress the web allows movement of the users jaws relative to each other, further alleviating discomfort.

The present disclosure also relates to a method of treating symptoms of SDB in a patient comprising the steps of;
  providing an oral appliance as disclosed in all aspects herein and causing the patient to wear the oral appliance whilst sleeping.

In one aspect, the SBD is snoring.

In another aspect, the SBD is OSA.

Suitably, the appliance is worn during sleep for a minimum of three hours, suitably four hours, suitably five hours or more.

In one embodiment of the method, the oral appliance is used in combination with a CPAP machine in which the CPAP machine is connected to the air inlet opening of the oral appliance for blowing air into the mouth.

This is different to conventional CPAP therapy in which air is blown into the nose. With the disclosed method, air can be introduced into the oral cavity. This allows patients with nasal congestion and/or obstruction who are incompatible with conventional CPAP to be able to use CPAP.

Further, the oral appliance is held in place by the teeth within the arch receiving channels and the seal is provided by the lips about either the air inlet member that forms part of the oral appliance that receives an air outlet adapter from the CPAP machine or an air outlet adapter from the CPAP machine receives the air outlet member of the oral appliance.

In this way, the use of conventional CPAP masks may be avoided. The oral appliance bypasses the nasal cavity and any obstruction therein.

Also disclosed herein is a combination comprising an oral appliance of any one of claims 1 to 14 and an adapter having an air inlet and an air outlet and an air passage between the air inlet and the air outlet, wherein the air outlet is configured for fluid communication with the air inlet opening of the appliance and the air inlet is configured for fluid communication with an air supply.

Further, as discussed above, the oral appliance locates the tongue in an elevated position bringing the mandible forward. Whilst not wishing to be bound by theory, it is believed that the combination of bringing the tongue and mandible forward may have a positive effect on the airway, thereby allowing CPAP to be applied with a lower pressure than would be required with a conventional CPAP interface.

CPAP pressure reduction may avoid or reduce undesirable side effects such as air in the stomach, stomach pain or gas. Still further, many patients find it difficult to exhale against the positive pressure of the CPAP.

Alternately the described device can also be used in conjunction with a nasal CPAP, therefore positively ventilating through the nose and mouth while simultaneously advancing the mandible and the tongue. This combination (trilevel) positive ventilation would also require far less PAP and therefor have less leakage, minimal need for tight straps and air via oral ventilation will have minimal restriction from the tongue. As opposed to most MAD appliances which require substantial mandibular advancement accompanied by the detrimental effects previously stated.

According to another aspect of the disclosure there is provided a method of treating symptoms of SDB in a patient comprising the steps of;
providing an oral appliance as disclosed in all aspects herein, fluidly connecting the air inlet member to a CPAP machine and causing air from to flow from the CPAP machine into the patient's mouth through the air inlet member and causing the patient to wear the oral appliance whilst sleeping.

DETAILED DESCRIPTION

Figure 1:
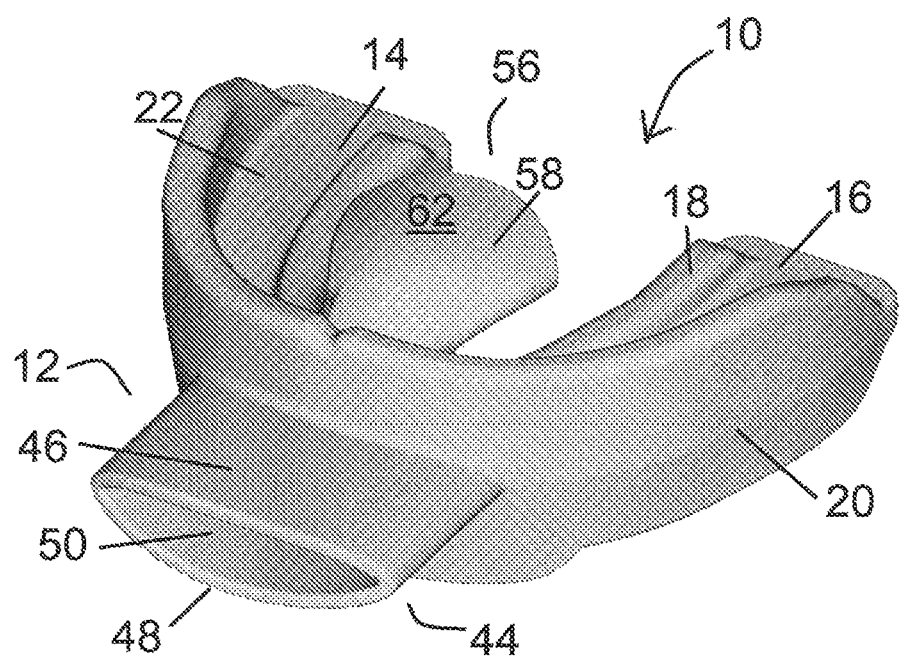
FIG. 1 is a top front perspective view of one aspect of an oral appliance as disclosed herein.

An oral appliance and methods in accordance with this disclosure may manifest itself in a variety of forms. It will be convenient to hereinafter describe several embodiments of the invention in detail with reference to the accompanying drawings. The purpose of providing this detailed description is to instruct persons having an interest in the subject matter of the invention how to carry the invention into practical effect. However it is to be clearly understood that the specific nature of this detailed description does not supersede the generality of the preceding broad disclosure.

FIGS. 1 to 8 show a first aspect of an oral appliance 10. The appliance 10 may be made of medical grade silicone that is a rubber material that is flexible and comfortable in the mouth. The flexibility can also accommodate users of different oral dimensions. The flexibility still further allows some movement that not only can provide comfort but can accommodate movement of the TMJ so as to reduce strain on the joint.

The appliance may also be made from a dual moulded having a base member that does not substantially soften at temperatures below 100° C. and a layer of a thermoplastic material such as ethylene vinyl acetate (EVA) that is softenable below 100° C. over the base member.

The base member may be a polyolefin such as polyethylene (PE), polypropylene (PP) or blends thereof. One example of a suitable polyolefin blend is a PE/polyurethane (PU) blend.

The base member confers a suitable level of rigidity on the base member but does have some flexibility and this enables the appliance to accommodate arches of varying width.

It will be appreciated that the flexibility allows for better fit whilst the mouldable outer layer provides a degree of customisation.

The appliance 10 includes a U shaped appliance body for mounting over the upper arch of a user. The appliance body 10 has a front section 12 and two arms 14, 16.

The appliance 10 includes an inner wall 18 that is positioned on a lingual side of the patient's upper arch and an outer wall 20 that is positioned on the buccal side thereof.

The outer wall 20 is U shaped with a front 20f and two arms 20a. The inner wall 18 is U shaped with a front 18f and two arms 18a.

The appliance body 10 also includes a U shaped web 22 interconnecting the inner wall 18 and the outer wall 20. When the appliance 10 is in the mouth of a user, the web 22 lies in the occlusal plane between the dentition of the upper and the lower arches in use.

Figure 4:
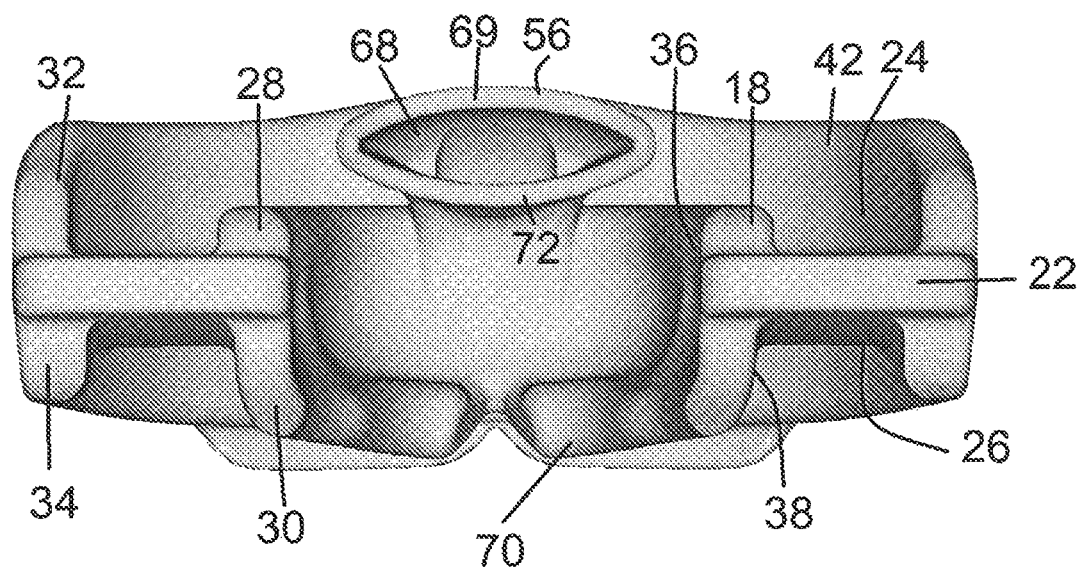
FIG. 4 is a rear view of the oral appliance shown in FIG. 1.
Figure 5:
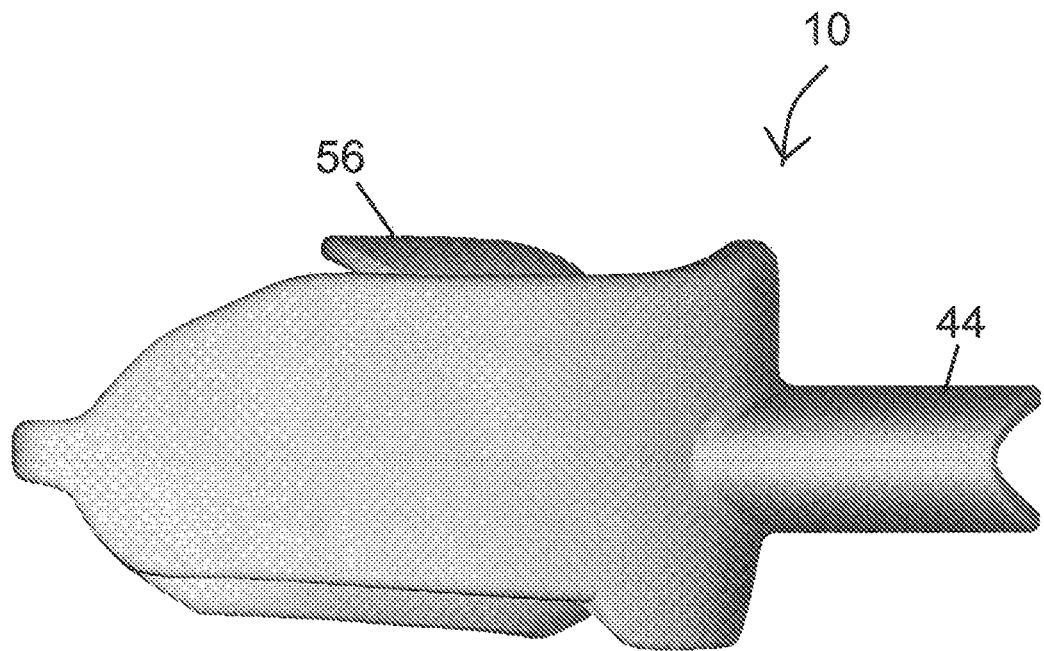
FIG. 5 is a side view of the oral appliance shown in FIG. 1.

The inner 18, outer wall 20 and web 22 define upper 24 and lower 26 arch receiving channels within which respectively the upper arch and associated dentition and the lower arch and associated dentition can be received (most clearly seen in FIG. 4).

The inner wall 18 includes an upper portion 28 which projects up from the web 22 and a lower portion 30 which projects down from the web 22. Similarly the outer wall 20 comprises an upper portion 32 above the web 22 and a lower portion 34 below the web 22.

The inner wall 18 has a lingual surface 36 and a channel surface 38.

The outer wall 20 has a front buccal surface 40 that is dimensioned so that it substantially covers the buccal aspects of the upper and lower posterior teeth.

Figure 3:
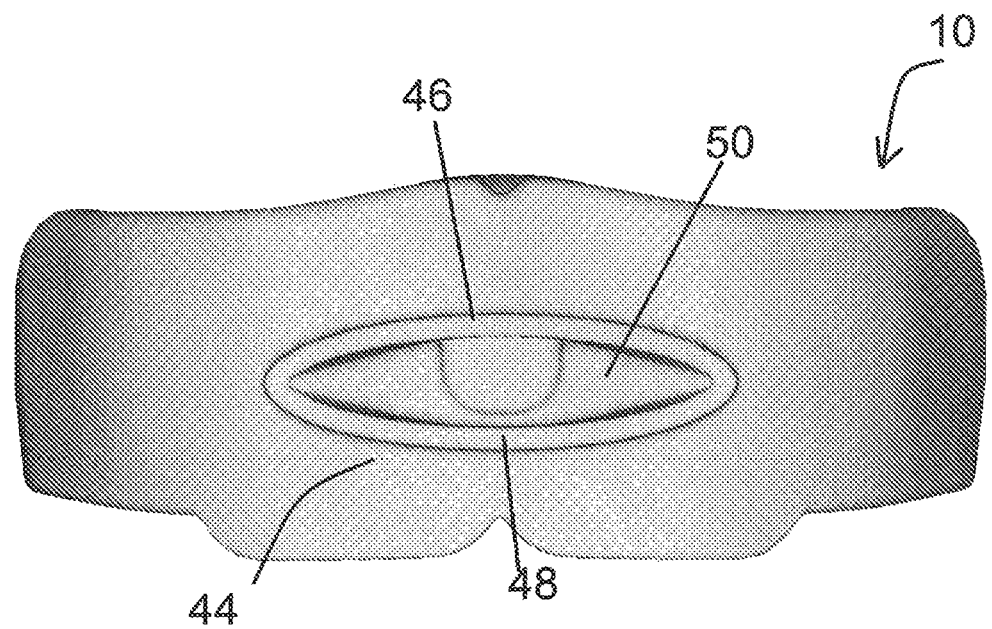
FIG. 3 is a front view of the oral appliance shown in FIG. 1.

The oral appliance 10 includes an air inlet member 44 extending forwardly from the front buccal surface 40 of the outer wall 20. The air inlet member 44 is may be any suitable shape or configuration and may be elliptical or ovoid in cross section and is located generally centrally on the buccal surface 40. The air inlet member 44 has a curved upper wall 46 and a curved lower wall 48 and an elliptical inlet 50 (as can be seen in FIG. 3). The inlet 50 is surrounded by a lip 52 (as seen in FIG. 6).

In another aspect, the air inlet may be ovoid. The air inlet may also comprises a plurality of inlet aperatures.

The curvature of the upper and lower walls 46, 48 of the air inlet member 44 is designed for a user's lips to fit comfortably around so as to be able to form a lip-seal around the air inlet member 44. This means that the only way that air can pass into the mouth is through the air inlet 50. It will be appreciated that other shapes or configurations of the air inlet member may be suitable for the purpose.

Figure 6:
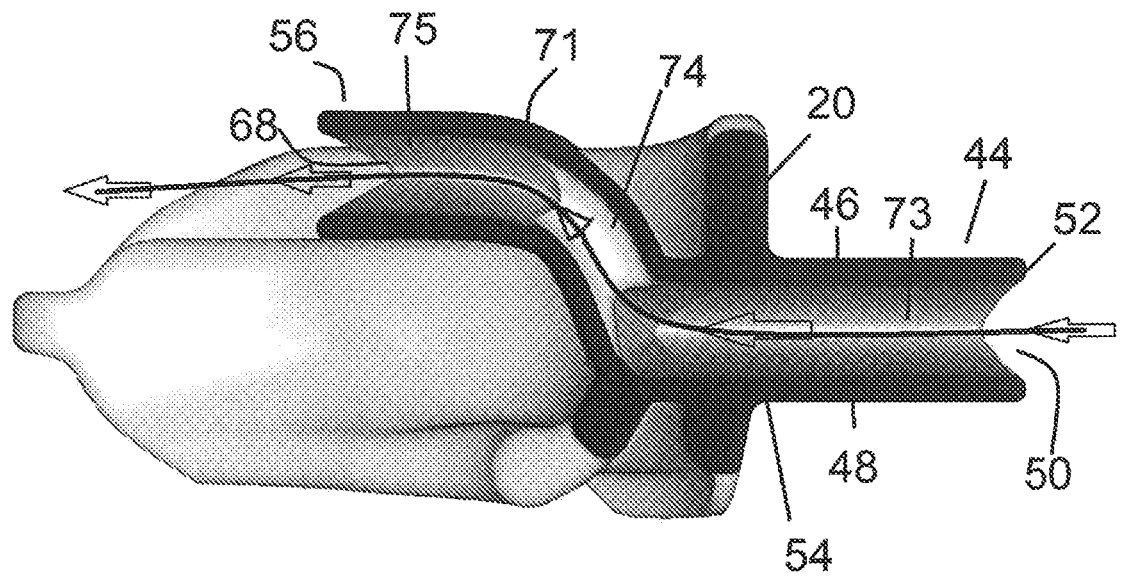
FIG. 6 is a cross section of the appliance shown in FIG. 1

As can be seen in the cross section in FIG. 6, the upper 46 and lower walls 48 define an air passage 54 that extends through the outer wall 20.

The frontal portion of the inner wall 18f inclines rearwardly away from the outer wall 20 as it extends up from the web 22 at an angle of about 30 to 40 degrees. This matches the curvature of the lingual side of the maxillary teeth.

Figure 2:
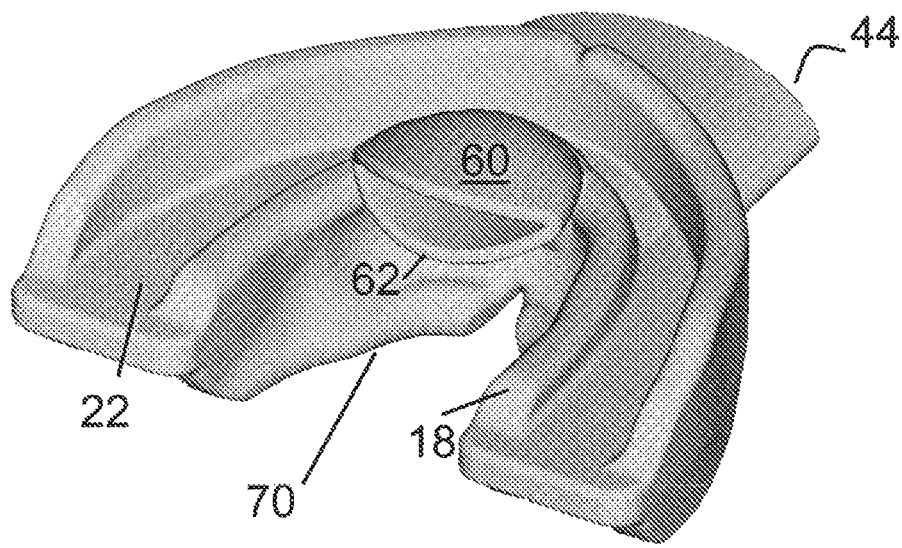
FIG. 2 is a rear top perspective view of the same oral appliance shown in FIG. 1.

The lower portion of the inner wall 18 includes a tongue elevator 70 (shown in FIGS. 2 and 4). The lower part 18l of the inner wall 18 has a lower terminal edge region that is thickened to form the tongue elevator 70. The tongue elevator 70 forces the tongue to hold an upwards position that further assists in bringing the tongue forward so as to open the airway.

At substantially centrally in the upper part 28 of the inner wall 18 there is a rearward facing extended part that forms an air outlet member 56. The air outlet member 56 has an outlet body 58. The outlet body 58 has an upper wall 60 that is concave in the transverse direction and a lower wall 62 that is also concave in the transverse direction.

Figure 7:
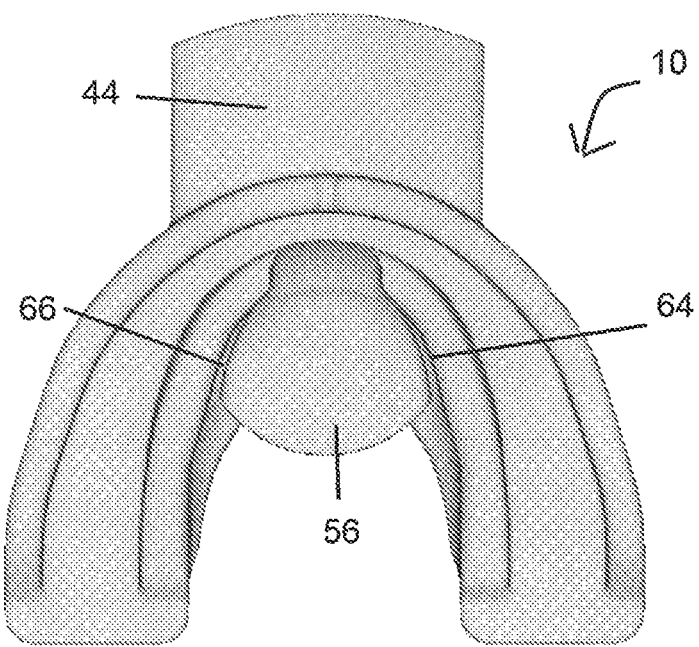
FIG. 7 is a top plan view of the oral appliance shown in FIG. 1.
Figure 8:
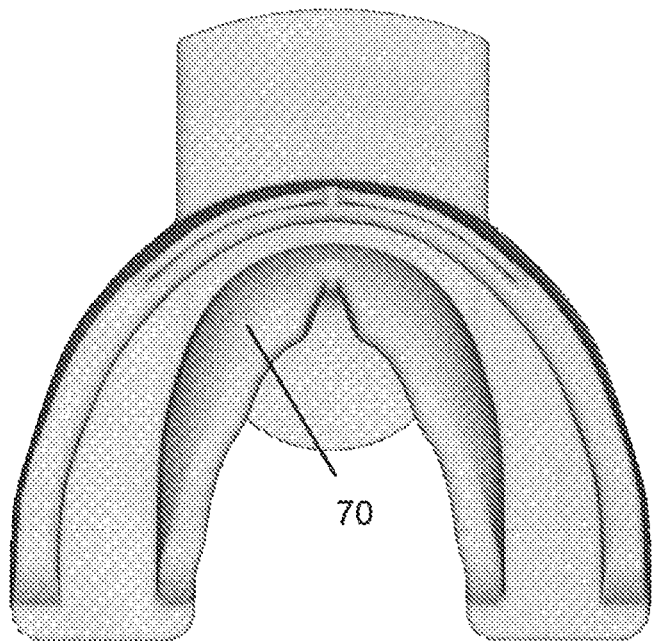
FIG. 8 is a bottom plan view of the oral appliance shown in FIG. 1.

The outlet body 58 further comprises opposing side edges 64, 66 and a posteriorly facing elliptical air outlet 68. As seen in FIG. 7, the side edges 64, 66 of the outlet body 58 diverge outwardly towards the air outlet 68. The elliptical outlet 68 has an upper edge 69 that is convex in the transverse direction and a lower edge 72 that is convex in the transverse direction. The outlet body 58 is also arcuate about a radial centre along the longitudinal axis of the body.

Figure 10:
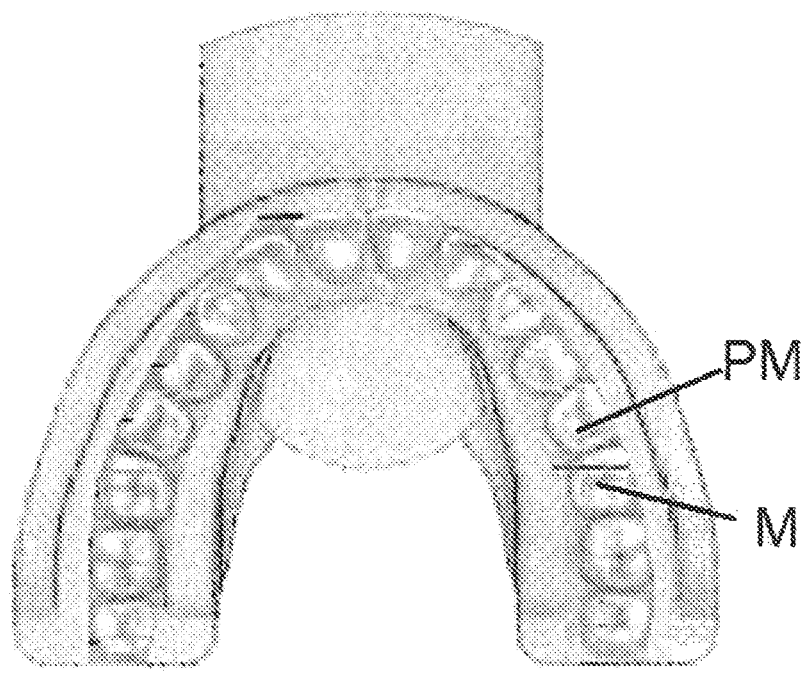
FIG. 10 is a schematic top plan view of the oral appliance shown in FIG. 1 and the relationship with the positions of the teeth of a patient's upper arch.

The air outlet member 56 is configured such that in use the air outlet locates horizontally adjacent or close to the hard palate at a position between the molars, suitably in the region of the second premolar PM and first molar M as shown in FIG. 10. This places the air outlet 68 above the tongue about the middle part of the hard palate.

The curvature of the upper wall 60 of the air outlet body 58 substantially corresponds to that of a user's hard palate for comfort.

The air outlet member 56 has a degree of resilience such that it may comfortably press against the patient's palate so as to prevent or obstruct air from passing above the air outlet member 56 and the palate during exhalation so as to optimise air flowing into the air outlet 68.

The air outlet 68 is configured to extend substantially across the width of the hard palate at that point. In this way air enters the oral cavity uniformly across the cavity.

An air flow passageway 71 is defined between the air inlet 50 and the air outlet 68. The air flow passageway 71 has an inlet part 73 defined by the air inlet member and an outlet part 75 defined by the air outlet member body 58. The oral appliance 10 includes a curved intermediate part of 74 of constant cross section. The part 74 has an inner facing part and an outer part. The inner part receives the tip of a user's tongue. The tongue is highly responsive to objects in the mouth and will haptically explore the air outlet member 56 and part 74. This further brings the tongue forward. Further advantages of this tongue placement will be described below.

The diameter of the intermediate part 74 is constant and about 6 mm to 8 mm. The width of the air inlet is about 23 mm to 26 mm.

Fluid flow through an abrupt constriction in a pipe results in a decrease in pressure of the fluid. Fluid flow also experiences a decrease in pressure when travelling through a bend in a pipe. Fluid pressure also drops when fluid flows through an abrupt expansion.

Whilst not wishing to be bound by theory, it is believed that the flow of air upon inhalation from the inlet member through the constriction in intermediate part 74 and the bend therein. This decrease in pressure results in a positive external pressure that may assist inhalation.

Figure 11:
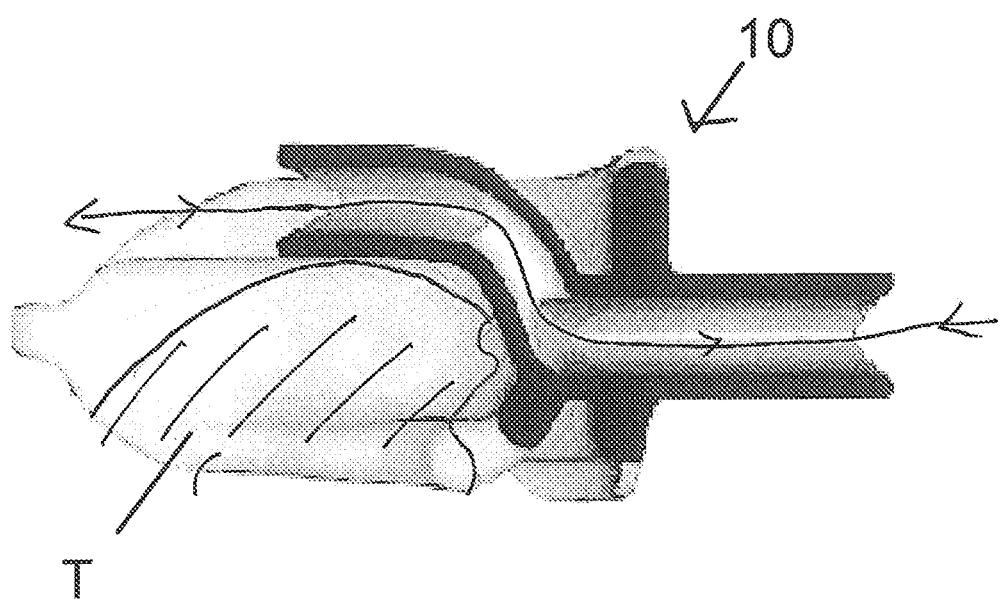
FIG. 11 is a schematic view of tongue position relative to the oral appliance of FIG. 1.
Figure 12:
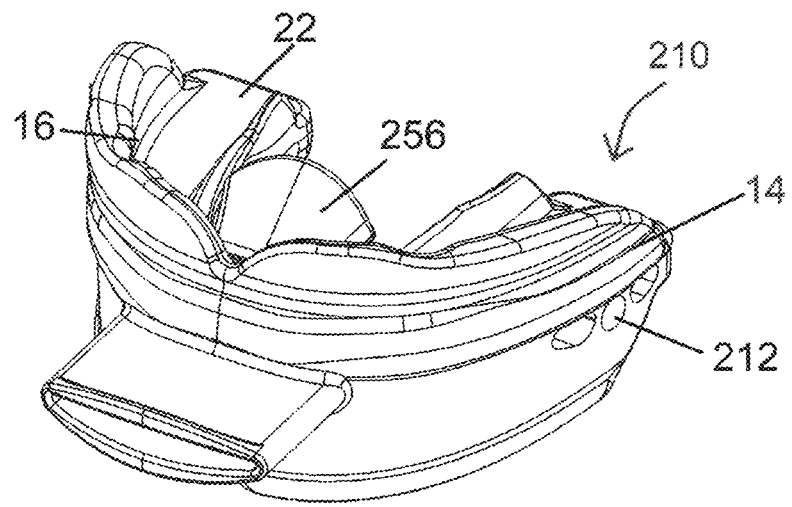
FIG. 12 is a front perspective view of an oral appliance of a still further disclosed aspect.
Figure 13:
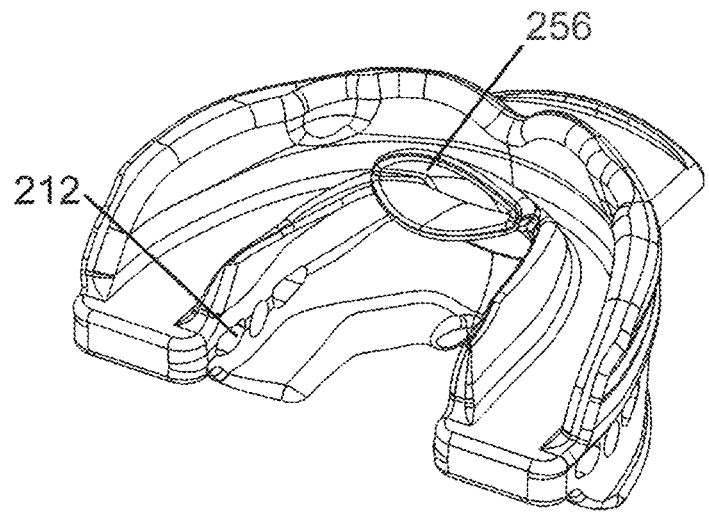
FIG. 13 is a rear perspective view of the oral appliance as shown in FIG. 12.
Figure 14:
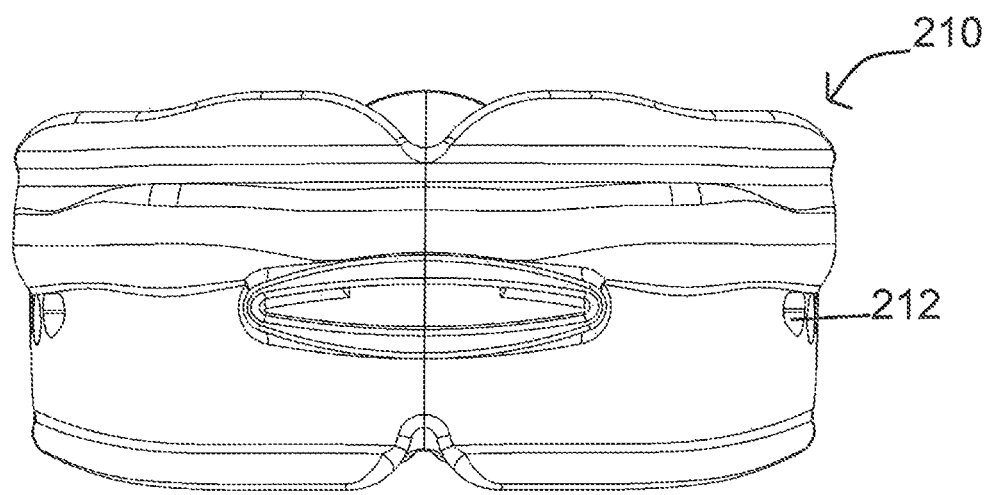
FIG. 14 is a front view of the oral appliance as shown in FIG. 12.
Figure 15:
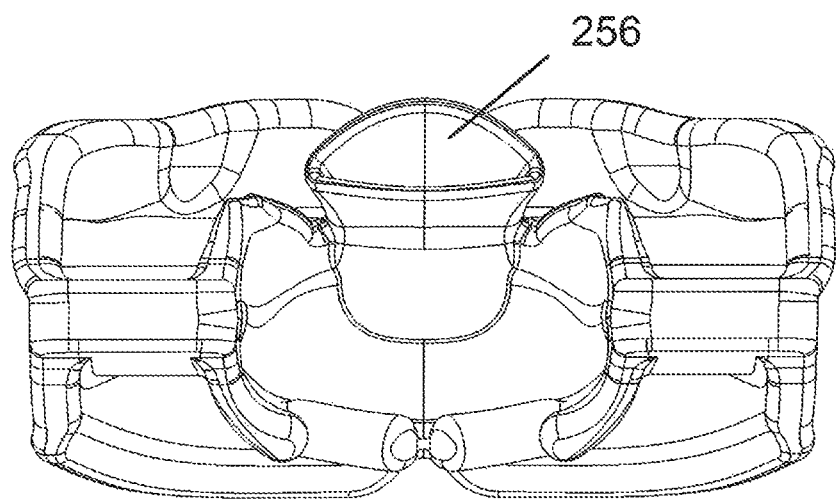
FIG. 15 is a rear view of the oral appliance as shown in FIG. 12.
Figure 16:
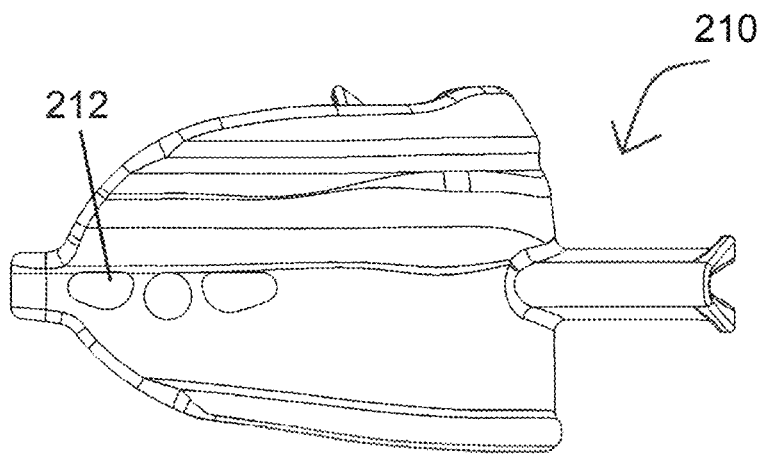
FIG. 16 is a side view of the oral appliance as shown in FIG. 12.

As discussed above, the oral appliance 10 encourages the tongue forward adjacent the air outlet member 56. This corresponds to the normal rest position nasal for breathing (subject to the thickness of the air outlet member). Under normal circumstances, such a tongue position would inhibit mouth breathing and the tongue would be forced into the lower position of a mouth breather in which the tip rests against the maxillary teeth. However, with the present appliance, air is delivered above the tongue at a position about half way along the hard palate and bypasses any such inhibition, whilst encouraging forward location of the tongue T. This is schematically shown in FIG. 11.

The air outlet member 56 is also flexible that allows the tongue to press up against it. A patient may be encouraged to do this so as to exercise and train the tongue to adopt the correct position, when the appliance is not being worn.

Whilst not wishing to be bound by theory it is believed that the positive pressure delivered to the mouth through the air outlet member 56 combined with shape and configuration of upper part of the air outlet member against the hard palette and further the activity of the tongue against the air outlet member 56 may assist in expansion of the maxilla. The lateral wall of each nasal cavity mainly consists of the maxilla. Thus expansion of the maxilla may increase the size of the nasal cavity, thereby reducing nasal obstruction. This in turn may over time alleviate at least partially the symptoms of OSA.

Figure 9:
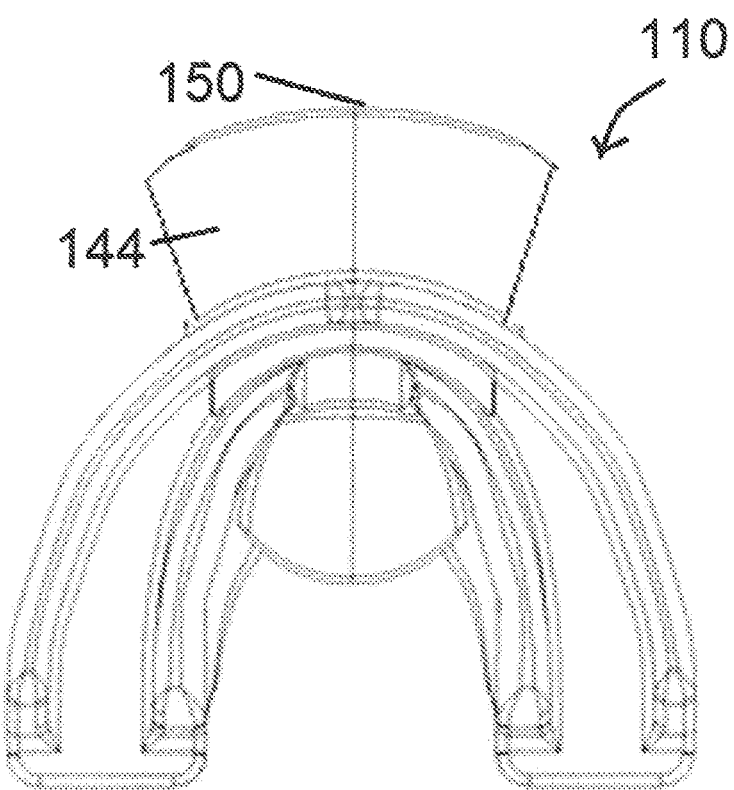
FIG. 9 is a top plan view of an oral appliance of a further disclosed aspect.

FIG. 9 shows an alternative oral appliance 110 in which the air inlet member 144 is tapered from the air inlet opening 150 towards the appliance 110.

Further the upper and lower arch receiving channels are configured for mandibular advancement (see FIG. 6). This physically brings the mandible and tongue forward and further opens the pharyngeal airway.

FIGS. 12 to 19 show an oral appliance 210 of another aspect of the disclosure. The same reference numbers will be used to define the same features.

The oral appliance 210 is substantially the same as the oral appliance of FIG. 1 with the addition of three compressible channels 212 in the web 22 of each arm 14, 16. The channels may be open or closed. The channels are compressible that further allows relative movement of the jaw so as to reduce strain on the TMJ.

Figure 17:
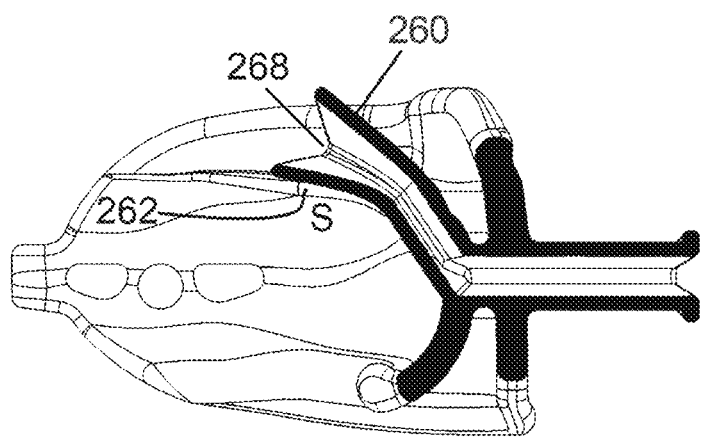
FIG. 17 is a cross section view of the oral appliance as shown in FIG. 12.
Figure 18:
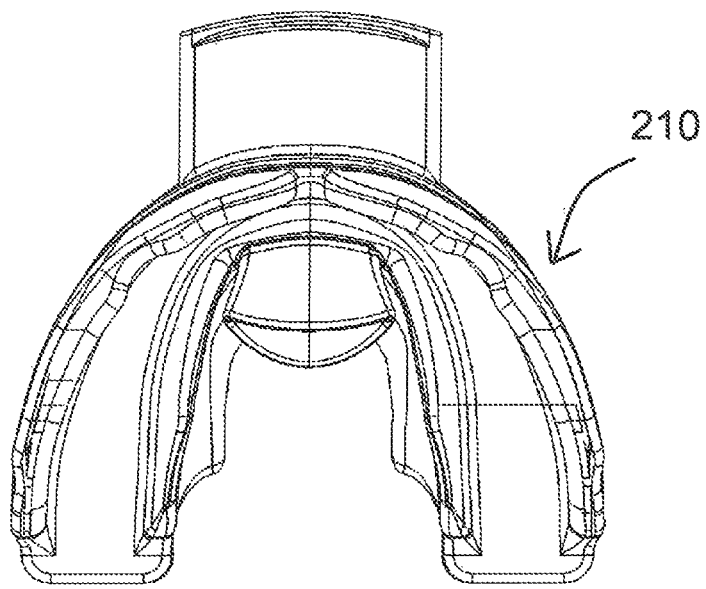
FIG. 18 is a top view of the oral appliance as shown in FIG. 12.
Figure 19:
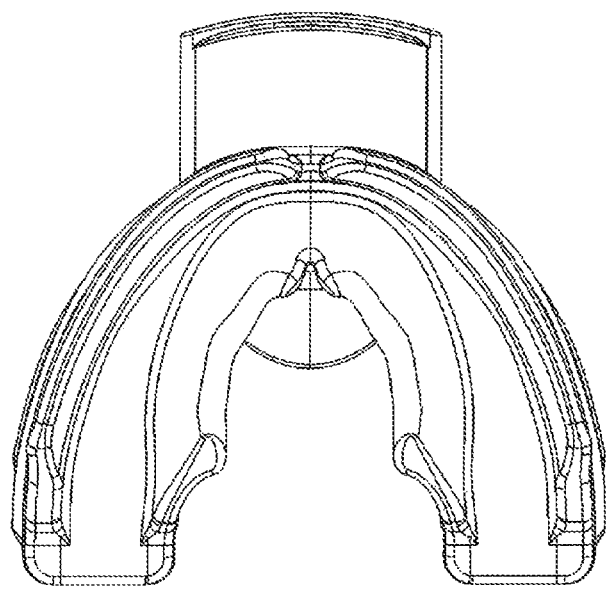
FIG. 19 is a bottom view of the oral appliance as shown in FIG. 12.

The air outlet member body 256 and the air outlet 268 each have a different configuration that may best be seen by comparing the cross section views in FIGS. 11 and 17.

Air outlet member body 256 has an upper wall 260 and a lower wall 262 that are diverging rather than parallel. The air outlet member body 256 is also at an angle of about 30 to 45 degrees to the horizontal rather than parallel. The air outlet body 256 is shorter and extends back to the premolars.

The space S where the tip of the tongue sits is larger than that in FIG. 11 that may facilitate further correct tongue placement.

Figure 20:
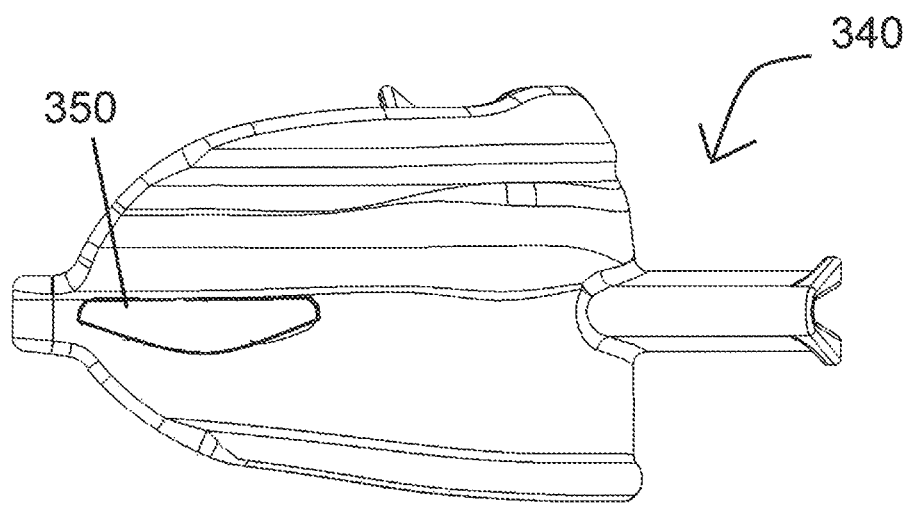
FIG. 20 is a cross section of a still further oral appliance as disclosed herein.
Figure 21:
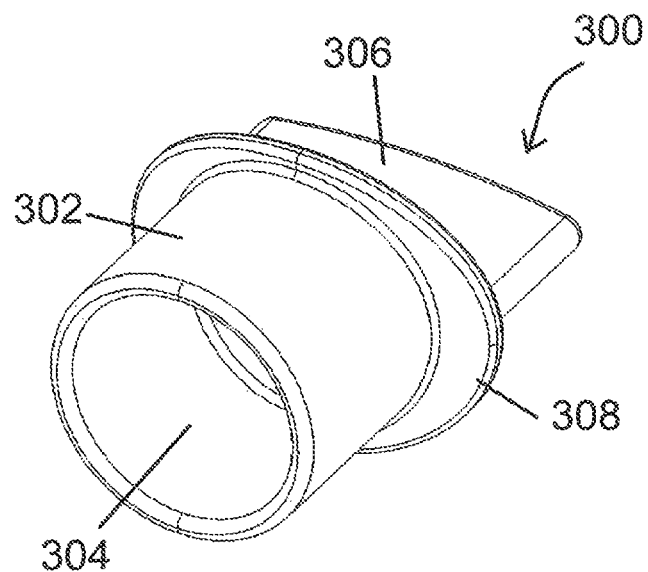
FIG. 21 is a front perspective view of a CPAP adapter for use with the disclosed oral appliances.
Figure 22:
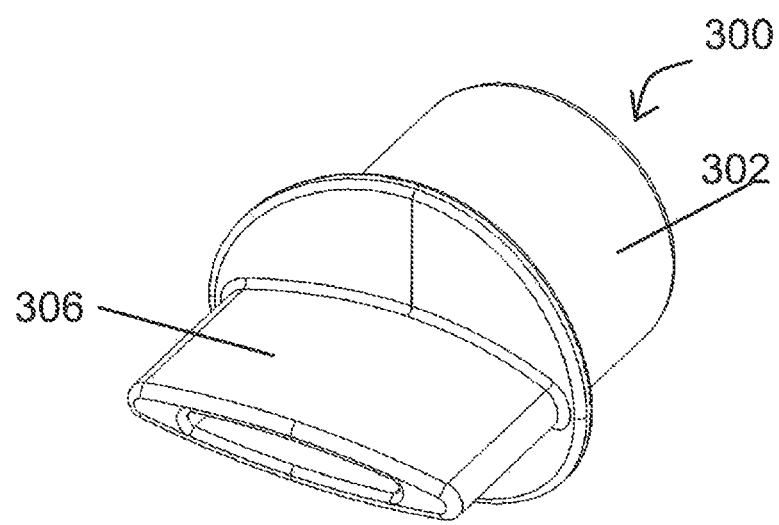
FIG. 22 is a rear perspective view of the adapter shown in FIG. 21.
Figure 23:
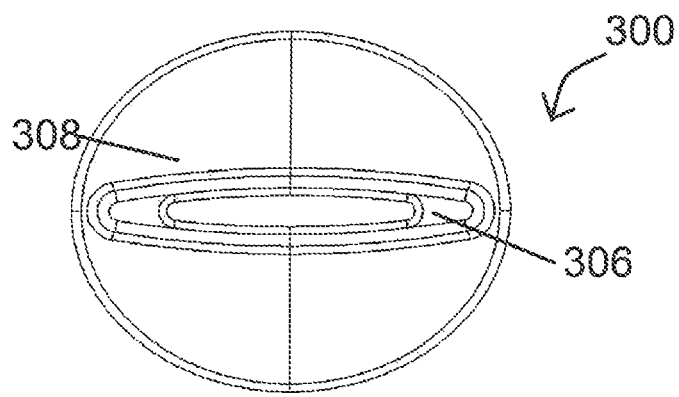
FIG. 23 is right end view of the adapter shown in FIG. 21.
Figure 24:
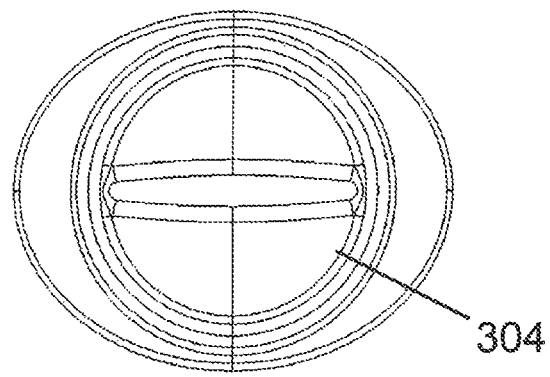
FIG. 24 is a left end view of the adapter shown in FIG. 21.
Figure 25:
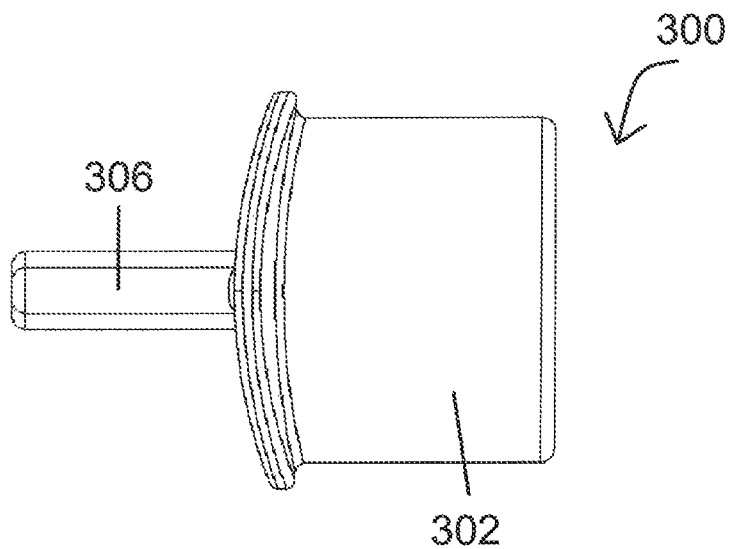
FIG. 25 is a side view of the adapter shown in FIG. 21.
Figure 26:
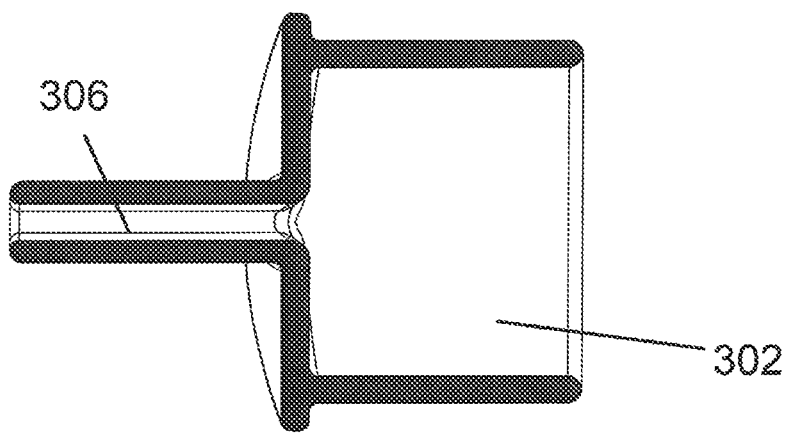
FIG. 26 is a cross section view of the adapter shown in FIG. 21.
Figure 27:
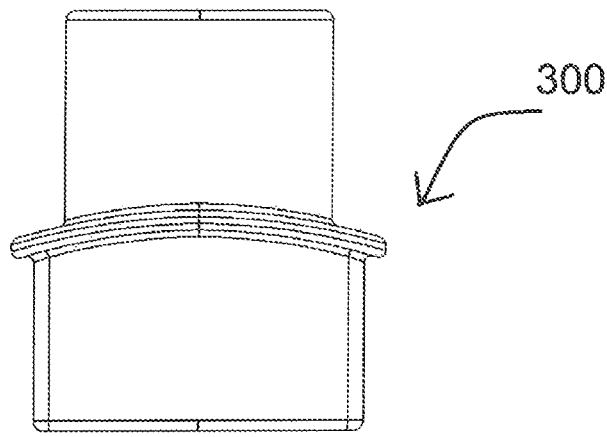
FIG. 27 is a top plan view of the adapter shown in FIG. 21.

FIG. 20 shows yet a further oral appliance 340 similar to that of FIGS. 12 to 19 but having a singular air channel 350.

FIGS. 21 to 26 show an adapter 300 that may be used to connect the oral appliance to an outlet tube of a CPAP machine.

The adapter 300 has cylindrical air inlet member 302 with an inlet 304. The inlet member 302 is configured for fluid connection to a CPAP air outlet tube. The inlet member 302 may receive or be received by the CPAP tube.

The adapter 300 has an outlet member 306 of elliptical cross section that is configured for fluid connection to the air inlet member 44 of the oral appliances 10, 210. The air inlet member 44 may receive or be received by the air outlet member 306.

The inlet member 302 and outlet member 306 are separated by an elliptical flange 308 that in use acts as a stop against a patient's lips.

Figure 28:
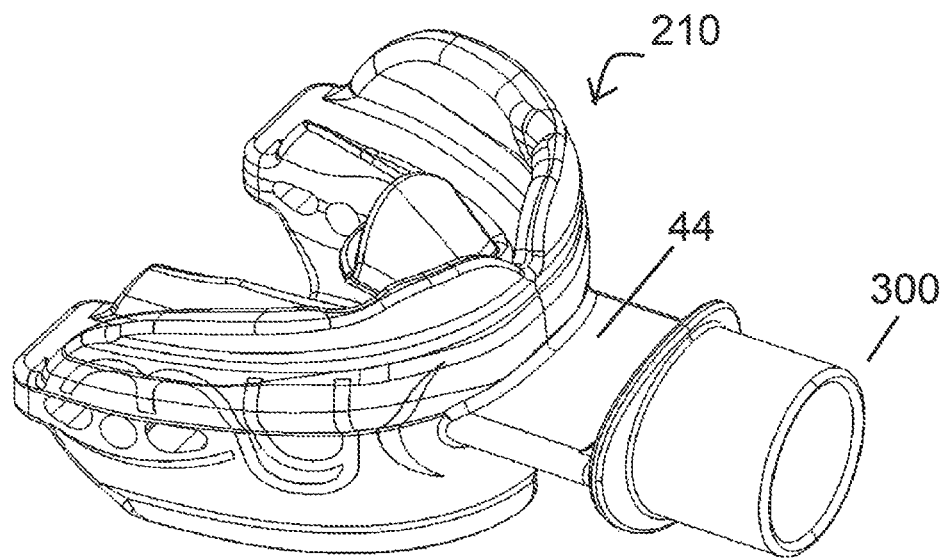
FIG. 28 is a front perspective view of the oral appliance as shown in FIG. 12 with the adapter as shown in FIG. 21 fitted thereto.
Figure 29:
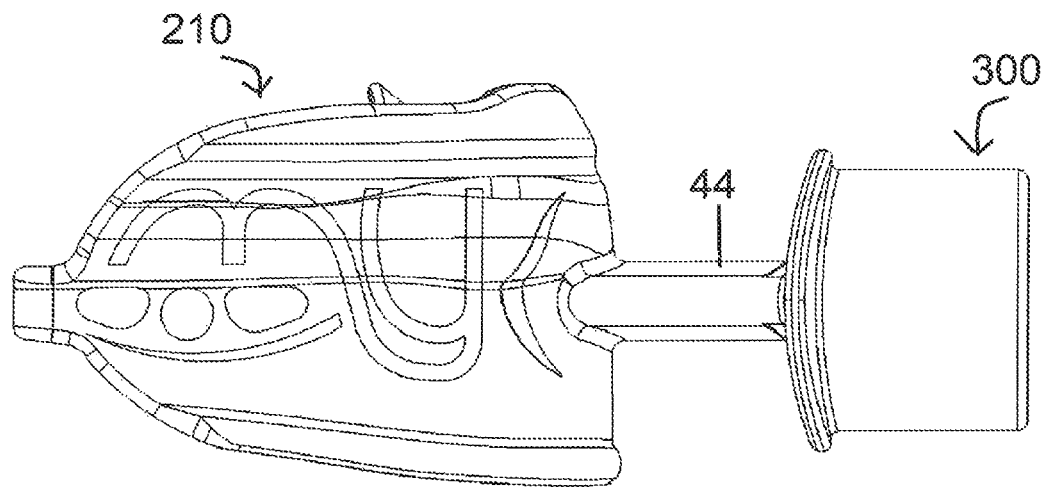
FIG. 29 is a side view of the oral appliance adapted combination as shown in FIG. 28.
Figure 30:
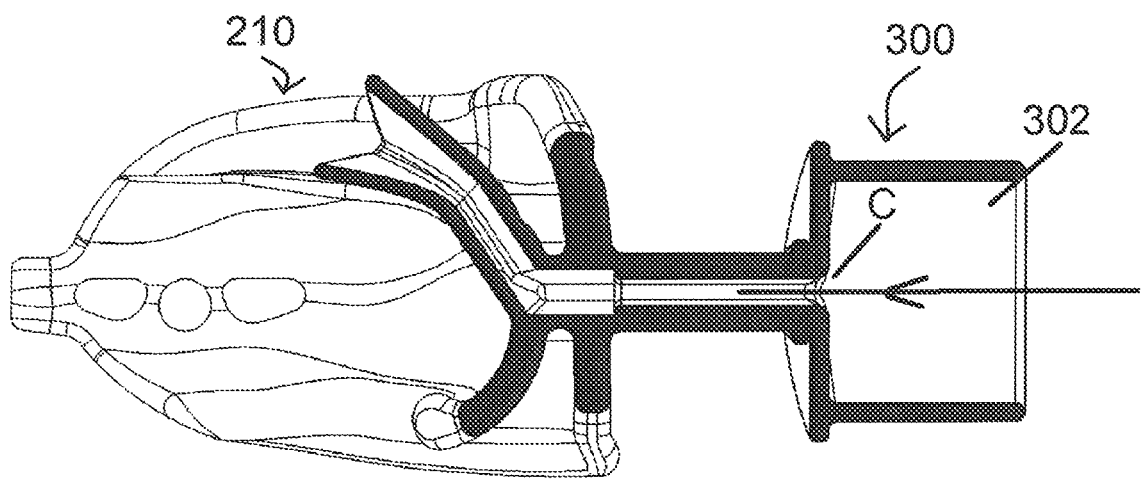
FIG. 30 is a cross section view of the oral appliance adapted combination as shown in FIG. 28.

FIGS. 28 to 30 show the adapter 300 connected to the appliance 210. It will be appreciated that such an arrangement may be more comfortable to a user than a nasal of full face mask. Seals against the face and chin straps are not required.

As can be seen in FIG. 30 there is a sudden contraction C in the in-flow direction from the air inlet member 302 to the air outlet member 306. Sudden contractions in pipes cause a marked drop in pressure due to an increase in velocity and loss of energy to turbulence.

Figure 31:
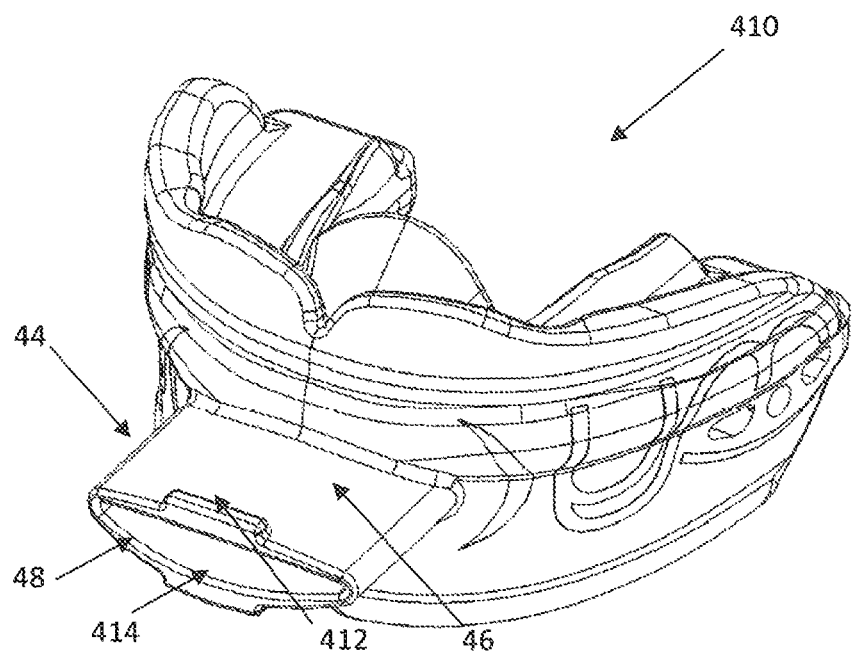
FIG. 31 is a front perspective view of another embodiment of an oral appliance as disclosed herein.
Figure 32:
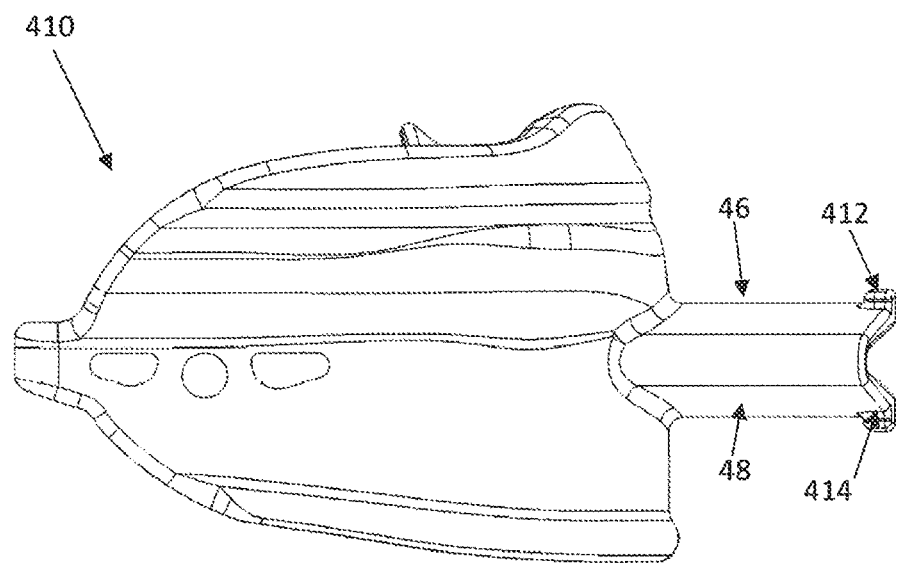
FIG. 32 is a side view of the oral appliance as shown in FIG. 31.

FIGS. 31 and 32 show an oral appliance 410 of another aspect of the disclosure. The same reference numbers will be used to define the same features.

The oral appliance 410 is substantially the same as the oral appliance of FIG. 1 with the addition of an upper tab 412 formed on the upper wall 46 of the air inlet 44, and a lower tab 414 formed on the lower wall 48 of the air inlet 44.

Figure 33:
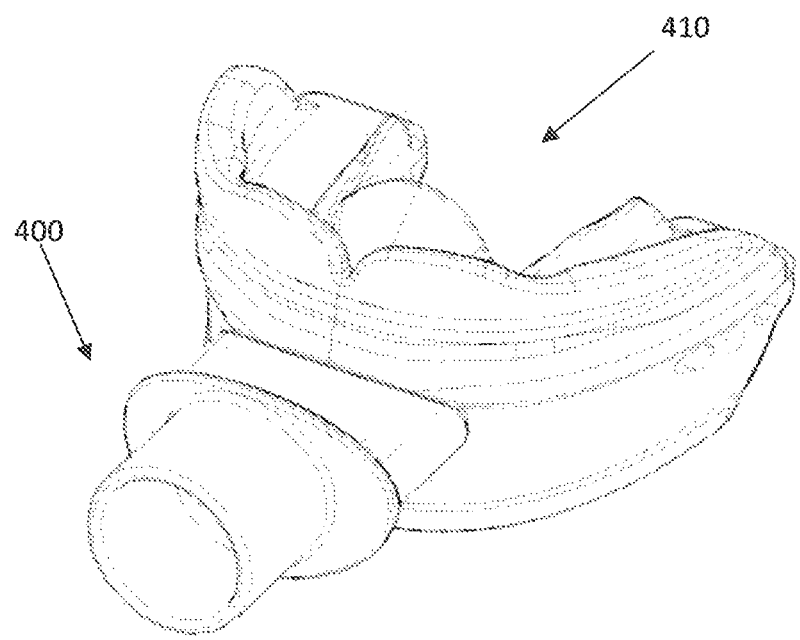
FIG. 33 is a front perspective view of the oral appliance as shown in FIG. 33 with a CPAP adapter fitted thereto and
FIG. 34 is a side view of the oral appliance as shown in FIG. 33 with the adapted shown in cross section.
Figure 34:
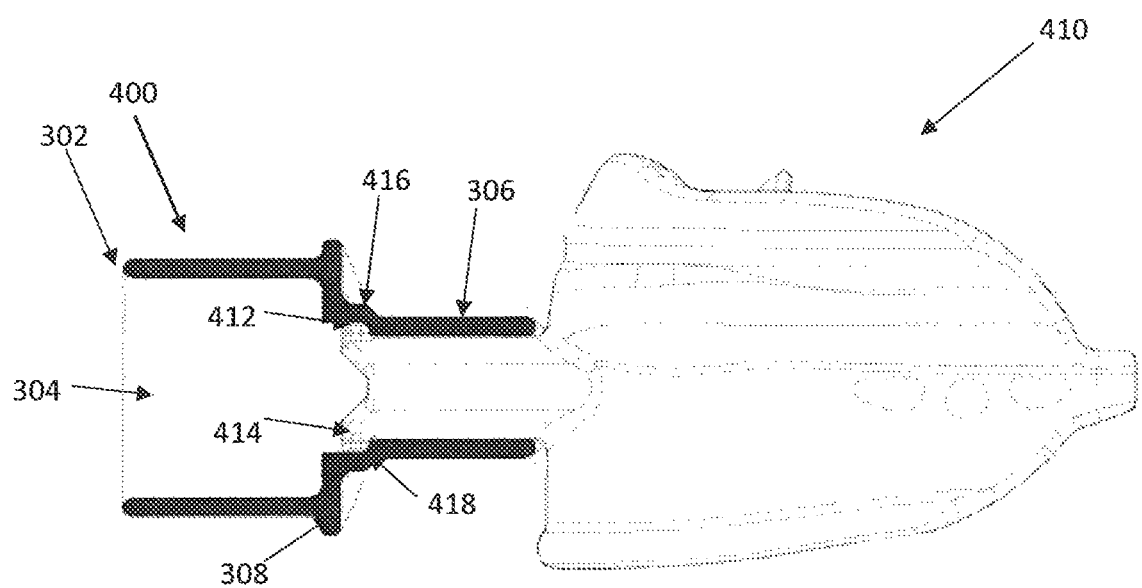

FIGS. 33 to 34 show an adapter 400 of another aspect connected to the appliance 410. The same reference numbers will be used to define the same features.

The adapter 400 is substantially the same as the adapter of FIGS. 21 to 26 with the addition of an upper groove 416 and a lower groove 418 formed on an internal surface of the outlet member 306, positioned adjacent to the elliptical flange 308. The upper recess 416 is configured to engage with the upper tab 412 of the oral appliance and the lower recess 428 is configured to engage with the lower tab 414 to thereby releasably secure the air inlet member 306 of the adapter 400 to the appliance 410. The walls of the adapter are sufficiently resilient so as to provide for a snap fit engagement with the appliance 410.

Mandibular advancement for a person having a normal bite will put some strain on the temporomandibular joints (TMJ). The flexibility of the silicone material or the material of a base member where the oral appliance is dual moulded allows some relative movement of the mandible that may at least partially alleviate such strain. However, this strain is significantly less than the art known MAD devices. Common side effects of art known MAD devices include TMJ discomfort or pain and myofascial pain. Long term advancement can cause TMJ damage and dysfunction.

The combination of forward tongue position and minimal mandibular advancement of the present appliances allows opening of the pharyngeal airway to extents comparable with known art MADs that significantly advance the mandible. Thus there is less strain on the TMJ with use of the present appliances than with art known MADs. This allows for more patient comfort which generally translates to higher patient compliance. This location of the tongue also reciprocates retrusive action of the maxilla.

The oral appliance may also be used in conjunction with a CPAP machine whereby the CPAP air tube is connected to the air outlet member.

It will be appreciated that the disclosed oral appliances do not require custom fabrication fitting by virtue of the flexibility of the thermoplastics material. The oral appliances may be easily manufactured by injection moulding at a fraction of the cost of custom made devices. Alternately, with the dual moulded ready-made device can be custom fitted with the above features.

The configuration of the air outlet member promotes voluntary forward positioning of the tongue that opens the airway. This may reduce the amount of mandibular advancement required. This in turn reduces stress on the TMJ. Stress on the TMJ is further reduced by the flexibility of the appliance.

It will be appreciated that various changes and modifications may be made to the appliances and methods as disclosed herein without departing from the spirit and scope thereof.

The invention claimed is:

1. An oral appliance for treating sleep disorder breathing (SDB) in a patient, the oral appliance comprising;
   a U-shaped appliance body with a anterior section and two arms, the U-shaped appliance body including an inner wall and an outer wall;
   a web interconnecting the inner wall and the outer wall so as to define an upper dental arch receiving channel;
   an air inlet member extending anteriorly of the anterior section of the U-shaped appliance body, the air inlet member defining an air inlet opening that is spaced from the U-shaped appliance body for intake of air;
   an air outlet member extending from an upper portion of the inner wall adapted to be located in the patient's mouth above the patient's tongue when in use, the air outlet member being configured to abut the patient's hard palate, the air outlet member comprising an air outlet configured for delivering the air inside the mouth wherein the air outlet member has a concave upper wall and a curved concave lower wall, and forms the air outlet having an elliptical configuration; and
   an air flow passageway comprising a curved intermediate part extending between the air inlet member and the air outlet member for communicating the air inlet opening with the air outlet, wherein the curved intermediate part curves upwardly and posteriorly to accommodate the patient's tongue.

2. The oral appliance of claim 1, wherein the air inlet opening is sized to have a cross sectional area for breathing that allows the patient to breathe through the patient's mouth.

3. The oral appliance of claim 1, wherein the air outlet member extends up at an angle of 30 to 45 degrees to an axis passing through the web of the U-shaped body.

4. The oral appliance of claim 1, wherein the air inlet member is configured to allow the patient's lips to form a seal about the air inlet member.

5. The oral appliance of claim 1, wherein the air inlet member has an elliptical configuration with a constant cross-sectional configurations along its length.

6. The oral appliance of claim 5, wherein the cross-sectional flow area of the air inlet member between the air inlet and the constricted part is between about 200 mm² to about 400 mm².

7. The oral appliance of claim 6, wherein the cross-sectional flow area of the constricted part is between about 50 mm² and about 100 mm².

8. The oral appliance of claim 1, wherein the air inlet member has an elliptical frusto-conical configuration comprising side walls that taper inward from the air inlet opening towards the appliance body.

9. The oral appliance of claim 1, wherein the air flow passageway has a constricted part between the air inlet member and the air outlet member.

10. The oral appliance of claim 1, wherein the curved upper and lower walls of the air outlet member diverge in a direction towards the air outlet, and the air outlet member has side edges that diverge in a direction towards the air outlet.

11. The oral appliance of claim 1, wherein the air outlet member has a degree of resilience such that it is adapted to resiliently contact or press against the patient's hard palate and direct inhaled air flow above the patient's tongue.

12. The oral appliance of claim 1, that further comprises a lower dental arch receiving channel, and wherein the upper and lower dental arch receiving channels are configured so that when the oral appliance is being worn, the patient's mandible is advanced.

13. The oral appliance of claim 12, wherein the patient's mandible is advanced a distance of 5 mm or less.

14. The oral appliance of claim 12, wherein the patient's mandible is advanced a distance of 1 mm to 3 mm.

15. A combination comprising an oral appliance of claim 1, and an adapter having an air inlet and an air outlet and an air passage between the air inlet and the air outlet, wherein the air outlet is configured for fluid communication with the air inlet opening of the appliance and the air inlet is configured for fluid communication with an air supply.

16. The combination of claim 15, wherein the adapter comprises an air inlet member configured for fluid connection to a CPAP air outlet and an outlet member configured to received or be received by the air inlet member of the appliance.

17. The combination of claim 16, wherein the adapter incudes a flange between the inlet member and the outlet member that in use acts as a stop against a patient's lips.

18. A method of treating symptoms of sleep disorder breathing (SDB) in a patient comprising:
   providing an oral appliance as disclosed in claim 1 and causing the patient to wear the oral appliance whilst sleeping.

19. The method of claim 18, wherein the SDB is snoring or obstructive sleep apnea (OSA), and the oral appliance is worn during sleep for at least three hours.

20. A method of treating symptoms of sleep disorder breathing (SDB) in a patient comprising:
   providing the oral appliance as claimed in claim 1,
   fluidly connecting the air inlet member of the oral appliance to a CPAP machine and causing air to flow from the CPAP machine into the patient's mouth through the air inlet member and causing the patient to wear the oral appliance whilst sleeping.

21. The oral appliance of claim 1, wherein the curved intermediate part has a smaller cross-sectional area for air flow therethrough than the air inlet member.

* * * * *